United States Patent [19]

Snyder et al.

[11] Patent Number: 4,686,999
[45] Date of Patent: Aug. 18, 1987

[54] MULTI-CHANNEL VENTILATION MONITOR AND METHOD

[75] Inventors: Leon T. Snyder; Frank A. Scarfone; James L. Reuss, all of Boca Raton; George V. Campen, Fort Lauderdale; George H. Yates, Boca Raton, all of Fla.

[73] Assignee: Tri Fund Research Corporation, Denver, Colo.

[21] Appl. No.: 753,069

[22] Filed: Apr. 10, 1985

[51] Int. Cl.[4] .................................................. A61B 5/08
[52] U.S. Cl. ...................................... 128/716; 128/671; 128/727; 128/723
[58] Field of Search ............... 128/670, 671, 721, 722, 128/723, 773, 716

[56] References Cited

U.S. PATENT DOCUMENTS

| | | | |
|---|---|---|---|
| 3,766,908 | 10/1973 | Haynes | 128/716 |
| 4,053,951 | 10/1977 | Hudspeth et al. | 128/670 |
| 4,116,228 | 9/1978 | Hudspeth et al. | 128/724 |
| 4,146,885 | 3/1979 | Lawson, Jr. | 128/721 |
| 4,169,462 | 10/1979 | Strube | 128/721 |
| 4,306,567 | 12/1981 | Krasner | 128/671 |
| 4,307,728 | 12/1981 | Walton | 128/722 |
| 4,356,825 | 11/1982 | Veth | 128/721 |
| 4,365,636 | 12/1982 | Barker | 128/716 |
| 4,449,537 | 5/1984 | Pross et al. | 128/723 |
| 4,474,185 | 10/1984 | Diamond | 128/722 |
| 4,475,558 | 10/1984 | Brock | 128/716 |
| 4,494,553 | 1/1985 | Sciarra et al. | 128/716 |
| 4,506,678 | 3/1985 | Russell et al. | 128/723 |

FOREIGN PATENT DOCUMENTS

3011770 10/1980 Sweden ............................ 128/773

OTHER PUBLICATIONS

Shiozawa et al, "ICU & CCU Systems of Nihon Kohden", Oct. 1970, pp. 75–77, Japan Electronic Engineering.

Katona et al, "Microprocessor-Controlled Memory for Cardiopulmonary Monitoring of High-Risk Infants", Nov. 1977, pp. 536–538, IEEE-Biomedical Engineering.

*Primary Examiner*—Edward M. Coven
*Attorney, Agent, or Firm*—John H. Faro

[57] ABSTRACT

The ventilation monitor of this invention includes a plurality of discrete sensors and a plurality of independent channels for processing the input signals from each of the discrete sensors. The principle category of sensor used in conjunction with this ventilation monitor is capable of the reception of information associated with breathing and cardiovascular movement. A second category of the sensor used in conjunction with this ventilation monitor is capable of the reception of audible sounds associated with breathing. Each of the individual input signals from these sensors is initially verified as being indicative of the sensation being monitored and, thereafter, compared in real time with one another and criteria stored within a microprocessor. The purpose of the comparison is to verify a normal breathing pattern and signal an alarm when the breathing pattern is abnormal. The ventilation monitor is also provided with means to dynamically adjust the gain and frequency response of each channel to accommodate changes in the monitored subject's position and physiological states.

14 Claims, 13 Drawing Figures

System Overview

Analyze
Cardiac
Signal

Analyze Mattress Respiratory Signal

Analyze
Audio Respiratory
Signal

Alarm
Update

Gain Check/ Adjustment

MULTI-CHANNEL VENTILATION MONITOR AND METHOD

BACKGROUND OF THE INVENTION

1. Field of the Invention

This invention is directed to an apparatus and to a method. More specifically, this invention concerns a multi-channel ventilation monitor and a method for real time monitoring of multiple signals associated with breathing and cardiovascular activity.

2. Description of the Prior Art

The monitoring of physiological activity of individuals with various types of instrumentation is an accepted method used by clinicians to detect abnormalities in biological functions. Monitors are available to measure cardiovascular activity, respiratory activity, and central nervous system activity. In the monitoring of physiological activity, a sensor is generally affixed to the individual and, in turn, connected to a signal interpreter. The signal interpreter can be relatively simple (i.e. U.S. Pat. No. 4,169,462—to Strube), or involve relatively simple and unsophisticated information processing (i.e. U.S. Pat. Nos. 4,306,567—to Krasner; and 4,356,825—to Veth).

In the device described by Strube, an electromechanical transducer, incorporating a piezoelectric crystal, is attached to the monitored subject. The transducer is used to detect variation in mechanical pressure resulting from breathing activity. Upon detection of such motion, the transducer relays an impulse, in the form of an electrical signal, to a counting circuit. An oscillator is associated with the counting circuit which in turn is preset to a predetermined counting period. The oscillator simply feeds a repetitive signal into the counter. If the transducer fails to generate a signal within a predetermined counting period to reset the counter, a switch is closed by the counting circuit which in turn triggers the alarm.

In the device described by Krasner, a sensor is attached to the monitored subject which is sensitive to acoustical signals indicative of a physiological rhythmic function. The Krasner device is designed to monitor acoustical signals within a relatively narrow frequency. These signals result from mechanical displacement of the body beneath the sensor. The design of the sensor and its attachment directly to the skin of the subject, is reputed to reduce the amount of spurious and environmental noise, in an attempt at enhancement of the signal-to-noise ratio. The electrical signal from the sensor is demodulated to enable detection of the periodic amplitude and modulated frequencies of the electrical signal. Once the signal has been reshaped or standardized, it is further processed to eliminate artifact within the predetermined acoustical frequency of interest. This further processing involves comparison of the duration of the demodulated signal, within the frequency bandwidth of interest, to a function rate signal. The Krasner monitor is designed to reject any signal within the frequency bandwidth of interest if it is less than or in excess of a predetermined signal duration (signals of less than 400 milliseconds duration and longer than 3-4 seconds being rejected as attributable to artifact). The relatively simplistic information processing logic of Krasner is thus unable to discriminate between true artifact and respiratory signals which may be outside the system parameters.

In the device described by Veth, a series of sensors are attached to the monitored patient for detection of different physiological activities (i.e. pulse rate, respiration and temperature). The data collected from these sensors is interpreted by a digital microprocessor associated with this electrical measuring system. This device is capable of intermittent measurement and processing of the input signal from only a single activity at any one time. The input signal is compared to a system clock, which utilizes a conventional oscillator (with an adjustable output frequency) as a standard. As is evident from the emphasis by Veth on rapid data analysis, his device is directed to an intermittent data sampling system. More specifically, the detection of successive data points is based upon a data sampling scheme involving the collection of a limited number of samples; the sampling interval and count frequency being controlled by a voltage controlled oscillator output signal. Accordingly, the Veth device is designed to restrict data sampling to a relatively brief period; with the data points being selected in this preselected interval and the interval being controlled by the voltage control oscillator.

The devices described hereinabove are fairly typical of those presently commercially available. Each of the above devices described by Krasner and Veth, respectively, share certain basic information processing similarities, (i.e. root mean square processing of signal data) as well as lack the ability to discriminate between apnea which is associated with obstruction of the breathing passageway from apnea which originates within the central nervous system (CNS). In addition, each of the foregoing devices lacks the ability to "effectively" distinguish between normal respiration and respiratory activity which may be indicative of an apnea episode. The reason for this deficiency is the inability of these systems to dynamically accommodate, or adjust, themselves to changes in the body position or the level of respiratory activity of the monitored subject. Thus, when the monitored subject is awake at the time monitoring commences, or is sleeping and progressively goes into a deeper sleep state, the level of physiological activity of the patient will change and the relative frequency of the signal will also change accordingly. When the sensitivity of the instrument is set to accommodate the intial activity state, it cannot effectively monitor the patient as the activity state becomes progressively more shallow. Attempts at overcoming this deficiency by setting the initial sensitivity at a very high level results in frequent false alarms and, thus, tends to impair the credibility of the monitor. The individual responsible for responding to such an alarm may not react quickly enough to intervene in a real emergency because of the skepticism which is created due to numerous false alarms. Conversely, where the sensitivity is set to accommodate the initial activity state, the monitor will be unable to effectively identify a true apnea episode requiring intervention as the physiological activity level becomes more shallow. Thus, there is a continuing need for improvement in respiration and ventilator monitors to reduce or eliminate the frequency of false alarms and yet provide effective monitoring of the patient at various and ever changing levels of respiratory activity.

OBJECTS OF THIS INVENTION

It is the object of this invention to remedy the above as well as related deficiencies in the prior art.

More specically, it is the principle object of this invention to provide a multi-channel ventilation monitor that is sensitive to distinct physiological activities indicative of respiration.

It is another object of this invention to provide a multi-channel ventilation monitor capable of real time monitoring of multiple signals indicative of respiration.

It is yet another object of this invention to provide a multi-channel ventilation monitor in which the sensors are not intimately attached to the monitored subject, nor incorporated into a garment or a harness that must be worn by the monitored subject.

It is still another object of this invention to provide a multi-channel ventilation monitor capable of real time monitoring of movement and sound indicative of respiration activity.

It is an additional object of this invention to provide a multi-channel ventilation monitor capable of dynamic adjustment of gain and frequency response for each of the sensed physiological activities to accommodate changes in the levels of each such activity.

It is yet an additional object of this invention to provide a multi-channel ventilation monitor which can identify an obstructive apnea episode.

It is still yet an additional object of this invention to provide a multi-channel ventilation monitor which can distinguish between obstructive apnea and an apnea episode which originates within the central nervous system (CNS).

It is a further object of this invention to provide a multi-channel ventilation monitor which incorporates both a base station and a portable unit, each of which can share data with the other which is accumulated as a result of independent monitoring the patient with either unit.

Further additional objects of this invention include the provision of an improved method for monitoring multiple physiological activities indicative of respiration.

SUMMARY OF THE INVENTION

The above and related objects are achieved by providing a multi-channel ventilation monitor for real-time monitoring of multiple physiological activities associated with breathing and cardiovascular activity. This ventilation monitor is provided with at least two (2) distinct types of sensors for monitoring physiological activity associated with breathing motion, cardiovascular motion, and the audible sounds associated with breathing activity. Each of the channels, which is responsible for processing the signal associated with each of these sensations, is independent of the other (i.e. motion signal processing being monitored on a channel which is separate and distinct from the channel dedicated to monitoring of audible information). This ventilation monitor is further unique in that the preferred system components need not be in intimate contact with the patient, (ie. no requirement that the sensor be incorporated within a harness or that an electrode be attached to the patient) and yet can still accommodate patient movement without loss or disruption of the ventilation monitoring function. This preferred system can thus be characterized as an "ambient" monitor; that is the monitoring of the patient is achieved by detection of physiological activity in the immediate environment of the patient.

In another of the preferred embodiments of this invention, the system includes the capability to dynamically adjust the sensitivity of the monitor to accommodate different levels of activity, (i.e. distinct sleep states) of the patient. This is achieved by real time comparison of the sensed input over a relatively brief interval, identifying a trend in the sensation which is being monitored and automatically adjusting the gain and frequency response to conform to this sensed trend. By continuously monitoring and adjusting the gain and frequency response to changes in the monitored sensation, as necessary, the sensitivity of the ventilation monitor can be maintained at its highest level while avoiding the occurrence of false alarms.

In another of the preferred embodiments of this invention, the system includes a piezoelectric transducer within a mattress which is used to detect physical movement associated with breathing activity and movement associated with cardiovascular activity (hereinafter referred to as "ballistic cardiogram" or "BCG"). The input signal from this single transducer is monitored for distinct signal frequencies characteristic of each such activity. This monitoring of both of these physical activities can be achieved without attachment of the piezoelectric transducer to the patient and is also independent of patient orientation and movement relative to the transducer.

In another of the preferred embodiments of this invention, the audible sounds associated with breathing are detected with either a directional microphone or with an array of microphones. The monitoring of audible sounds associated with breathing activity permits discrimination between obstructive apnea and CNS apnea. The microphone array is preferred because of its ability to differentiate background noise (i.e. sounds associated with the ambient environment) from sounds indicative of breathing activity.

In yet another of the preferred embodiments of this invention, the monitor consists of two separate units which are integral with one another and yet each capable of independent operation. For ease of differentiation, one unit is referred to as the "main or base station" and the second unit is referred to as the "module or portable unit". This portable unit is "docked" within the base station. In practice, the patient (typically an infant) is monitored in its crib at home or in the hospital utilizing the main station. The data acquired during this monitoring activity is shared with the portable unit which can then be used to continue such monitoring away from the home or hospital environment. The data acquired by the portable unit is retained by it and later shared with the main station when the two monitors are reunited.

DESCRIPTION OF THE INVENTION INCLUDING PREFERRED EMBODIMENTS

FIGS. 1(a) to (d) are a series block diagrams depicting the overall interrelationship of the components of the multi-channel ventilation monitor of this invention. As is evident from these diagrams, the device illustrated in FIG. 1(a) has only three (3) channels; however, this diagram is only illustrative and is not to be construed as indicative of limits of this system, or of the signal processing capabilities of this invention. For example, additional channels can be added to the system to process signals from a temperature sensor and/or from a transcutaneous sensor for $PO_2$ or $PCO_2$.

Figure 1A:
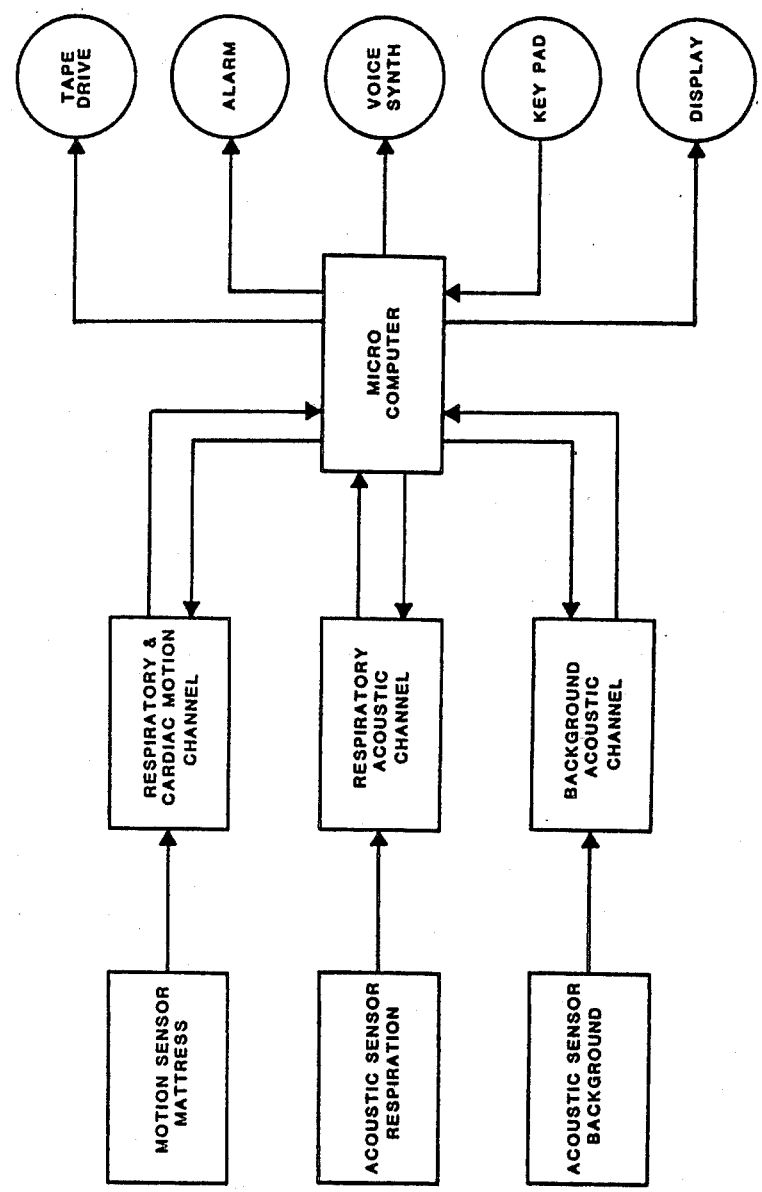
FIGS. 1(a) to (d) are a series of diagrams illustrating the relationship of the various components of the multi-channel ventilation monitor of this invention.
Figure 1B:
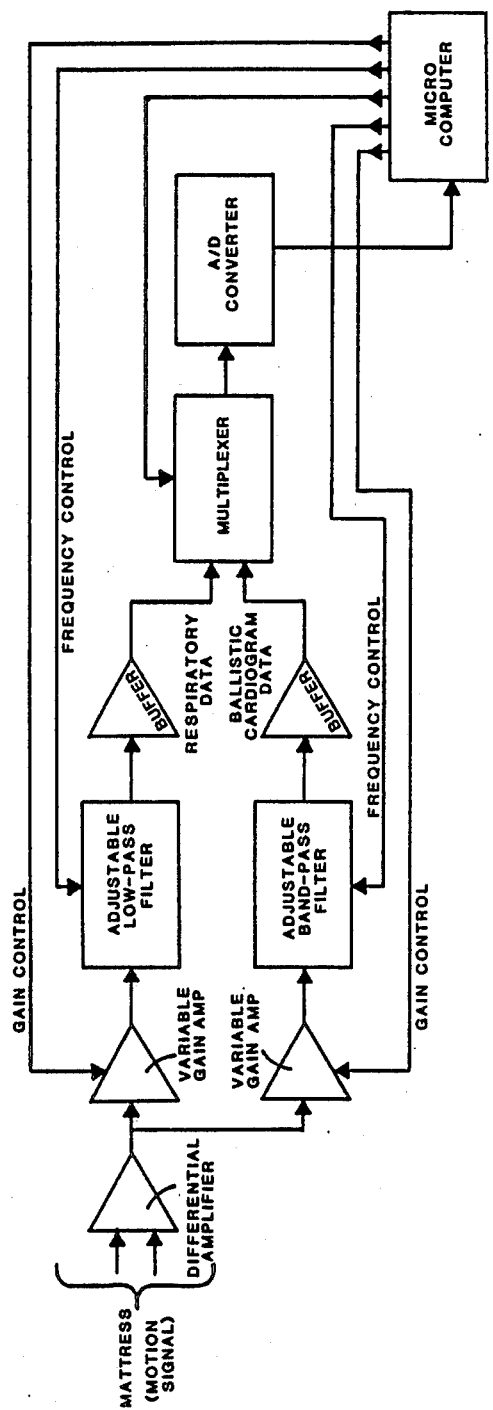
Figure 1C:
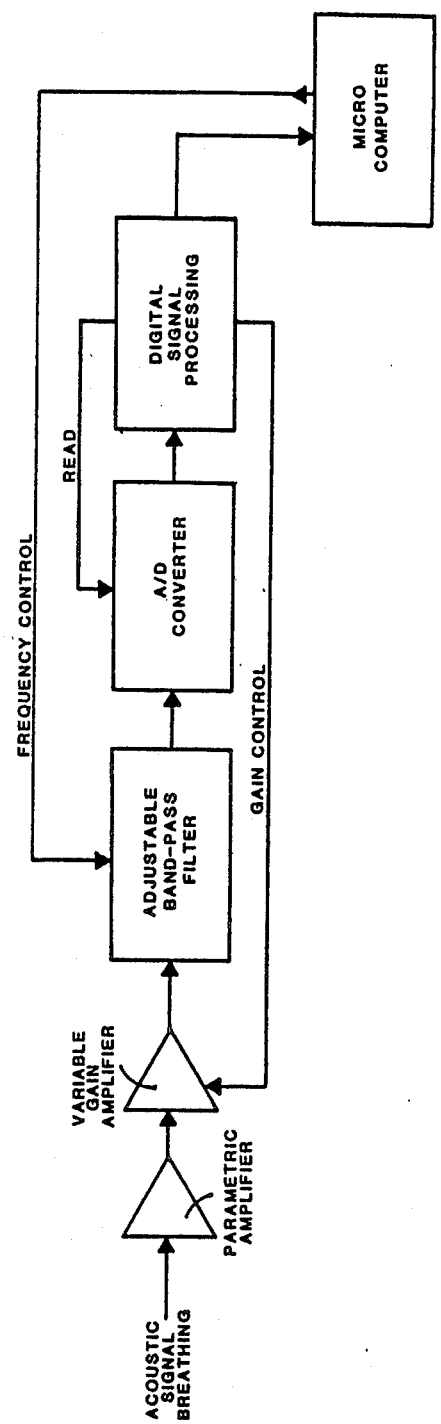
Figure 1D:
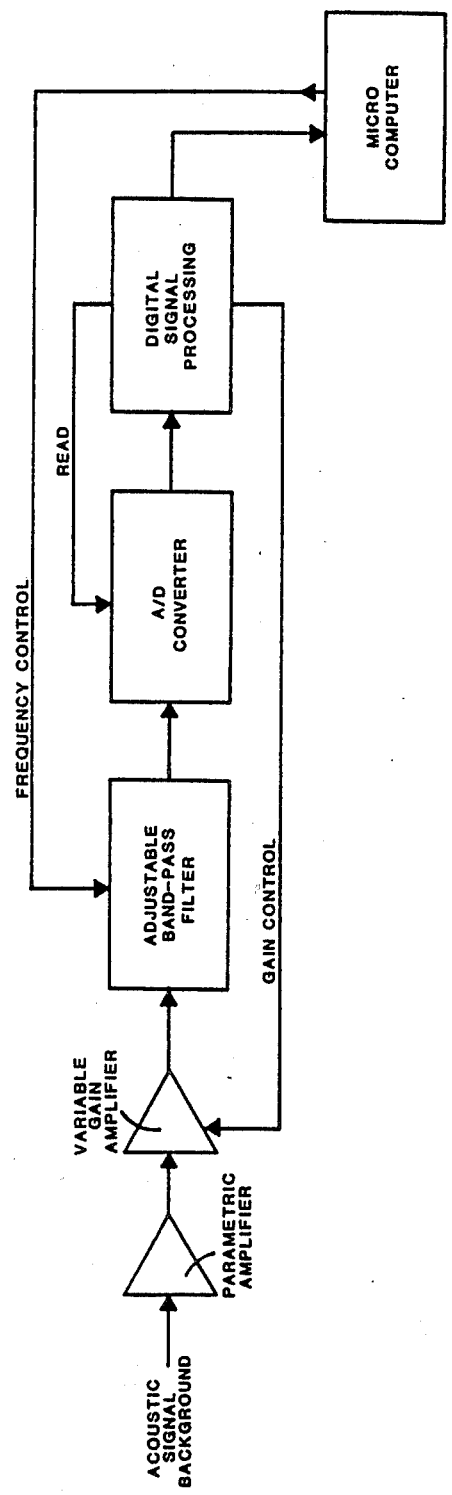

As more fully illustrated in FIGS. 1(b)–(d), input signals from a series of sensors generate distinctive electrical signals which are amplified, filtered, converted from analog to digital information and thereafter manipulated by a microprocessor. One of the unique aspects of this invention is the ability of the microprocessor to dynamically adjust the gain of the variable amplifiers in response to changes in the level of the monitored activity. More specifically, where an infant is monitored continuously, the body position and monitored level of physiological activity, (i.e. distinct sleep states) will change and the relative level of sensitivity of the monitor must be adjusted accordingly. In the signal processing channel illustrated in FIG. 1(b), such adjustment occurs automatically. Similarly, dynamic adjustment of the low pass and band-pass filters is also performed automatically in response to changes in activity levels. Both the variable gain amplifier and the adjustable low-pass and band-pass filters are under microprocessor control and such adjustment is made in response to information received and stored in the microprocessor.

The monitor of FIG. 1(a) utilizes both a motion sensor and two (2) acoustical sensors. The motion sensor of FIG. 1(b) of this device is preferably incorporated within the mattress. Movement by the subject laying upon the mattress will result in generation of electrical signals by a transducer within the mattress, (i.e. piezoelectric film of polyvinylidine fluoride). The electrical signals which are of interest include the patient's movements associated with respiration and subtle patient movements associated with cardiovascular activity. The electrical signal from this transducer is amplified by a differential amplifier and the signal frequency band associated with respiration and signal frequency band associated with cardiovascular motion are processed independently of each other through separate band pass filters which are under microprocessor control. The analog input voltage from each channel is then driven by a buffer to an analog multiplexer, where the analog input voltages from each signal is sampled in turn, converted into digital quantities by the analog to digital converter and communicated to the microprocessor. The response and control of the microprocessor over this information will be discussed in detail in review to the microprocessor system logic. The communication of this information to the microprocessor enables dynamic system control over both the variable gain amplifier and adjustable band pass filters.

The two other channels illustrated in FIGS. 1(c)–(d) are designed to process an input signal from acoustical sensors. Both channels are virtually the same, except for the frequency which each monitors; one channel being dedicated to processing of an acoustic signal at a frequency band indicative of breathing activity (for the detection of "obstructive APNEA"), and the other channel being dedicated to the processing of an acoustical signal at a frequency band indicative of background (off-center impulsive noise). The acoustical signal is initially passed through a parametric amplifier for low noise amplification, the signal voltage adjusted by variation in the amplifier gain, filtered and the analog voltage converted to digital quantities. The digital signal is further filtered through a digital signal processor. The digital signal processor contains a speech recognition chip. The combined output from these components is the derivation of a set of coefficients (linear predictive coding coefficients or LPC coefficients) which are analyzed by the main processor for breathing pattern recognition.

As will become evident from the discussion of the system processing logic, the programmed microprocessor of the monitor provides a degree of control over physiological signal data processing not heretofore available. The microprocessor functions include: (1) continuous monitoring of the input signals from each of these sensors; (2) continuous updating of its own data base on the monitored individual to detect trends in the physiological activities; (3) dynamic adjustment of the gain of the variable gain amplifier to accommodate changes in the level of physiological activity and dynamic adjustment of the various filters (band pass and low pass filters) to compensate for changes in signal frequency content incidental to such activity level variations; (4) analyzing the wave form of the input signal for characteristic shapes associated with abnormal breathing activity; (5) continuous monitoring of the system performance and operation for malfunctions; and, (6) altering the clinician or parent to apnea episodes requiring intervention and to system malfunctions which can adversely affect the integrity of the monitoring process.

As shown in the block diagram of FIG. 1(a), the microprocessor controls not only the various system functions and an alarm, but also a speech synthesizer which produces an audible message to alert the clinician or parent to the nature of the system response to a monitored event, (i.e. emergency requiring intervention or a system malfunction). The synthesized message can also provide instructions to the individual overseeing the monitor performance.

Other peripheral equipment illustrated in FIG. 1, includes a digital tape drive for preserving a record of the patient's physiological activities. The tape record is available for independent analysis by the clinician at a later date to enable him to periodically redefine the parameters within which the monitor is to operate. The term "parameter" as used herein is intended to include, in the broadest sense, any value under control of an algorithm, or a physician-defined limit, i.e. physiological limits which are prescribed by the clinician for an individual patient and which define a range of normal physiological activity.

Typically, the system will be set by the clinician to monitor a physiological activity with upper and lower limits on the average rate. For example, the respiratory rate range for newborns might be defined as 30-60 breaths per minute, and the heart rate defined as a rate range of 100-140 beats per minute.

A rate range may be periodically redefined by the clinician or parent by simply keying in the new parameters on the key pad provided for that purpose. An alpha numeric display is further provided with a menu of instructions for redefining these parameters, and can also be addressed by the microprocessor to display any one of a number of messages (e.g. emergency phone numbers and the like) or such other data which has been or is being collected by the system.

Figure 2:
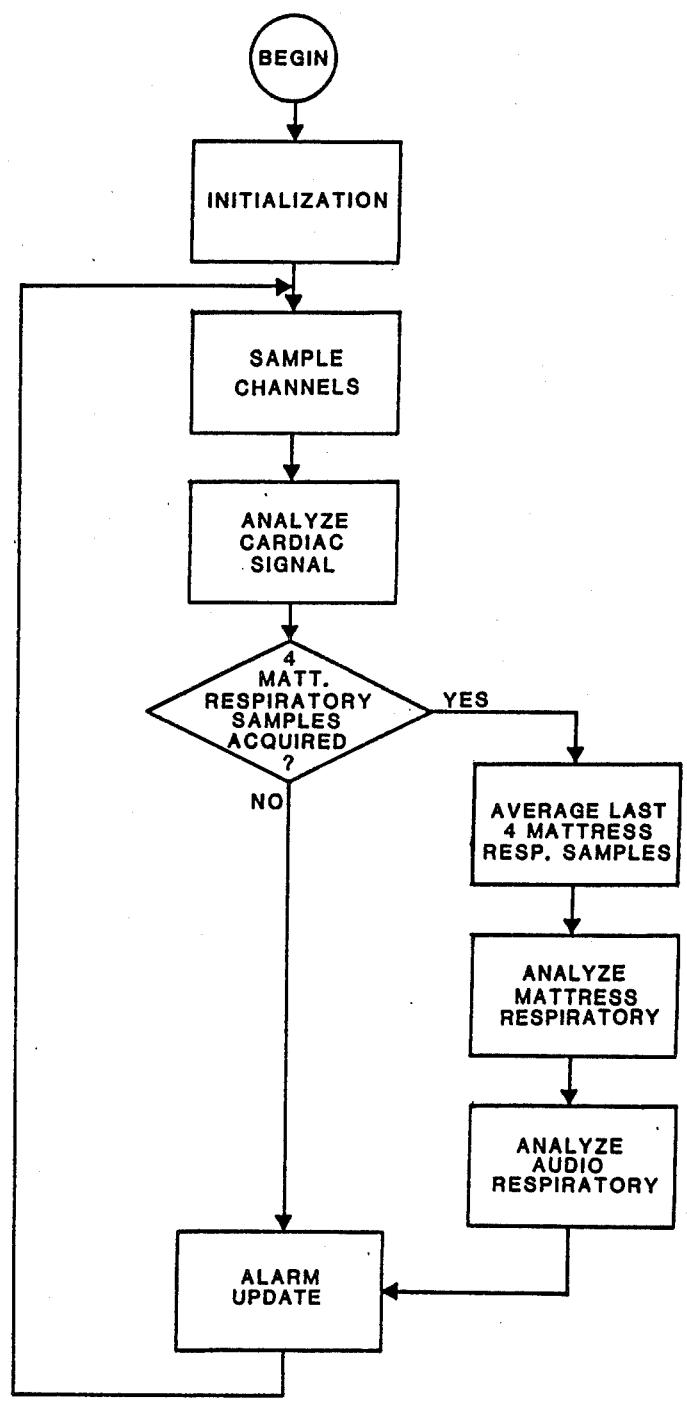
FIG. 2 is a flow diagram illustrating the signal processing logic of the multi-channel ventilation monitor of this invention.

FIG. 2 provides a flow diagram illustrating an overview of the system processing logic of the multi-channel ventilation monitor which is represented in FIG. 1. It is again emphasized that the limited number of physiological activities which are monitored in this illustration is not to be construed as indicative of the breadth of this invention. Additional physiological activities could also have been included within this illustration, but to do so would introduce additional complexities without enhancement in the ease of understanding or the ultimate level of comprehension.

In brief, the system logic of this device undergoes "initialization", or what can loosely be described to as "self-test" (lower level system check). This is achieved by setting the various system functions to known states and then confirming that each such system function accurately reflects such known values. Once the system is calibrated in the foregoing manner, it initiates multiple sampling of input signals from each of the discrete system channels.

The rate of sampling of signal input will differ depending upon the type of sensor which is used to monitor the individual physiological activity. Generally, the input signals which change at a more rapid rate are sampled more frequently than the input signals which change at a relatively lower rate. In the context of the system described in FIG. 1, the motion sensor is sampled twenty (20) times per second. In the logic diagram of FIG. 2, the respiratory signal is averaged after each four (4) samples of data is received reducing the effective sampling rate to five (5) times per second to provide a more accurate signal trend. Acoustic data is sampled at 6,000 samples per second before digital signal processing derives a set of coefficients (LPC coefficients) which refines the signal to relatively small set of numbers which are representative of predominant frequencies of signal (e.g. derived 20 times per second). The frequency of sampling is an algorithm defined parameter and can be increased or decreased depending upon the system capabilities to process and assimilate the signal input.

Figure 6:
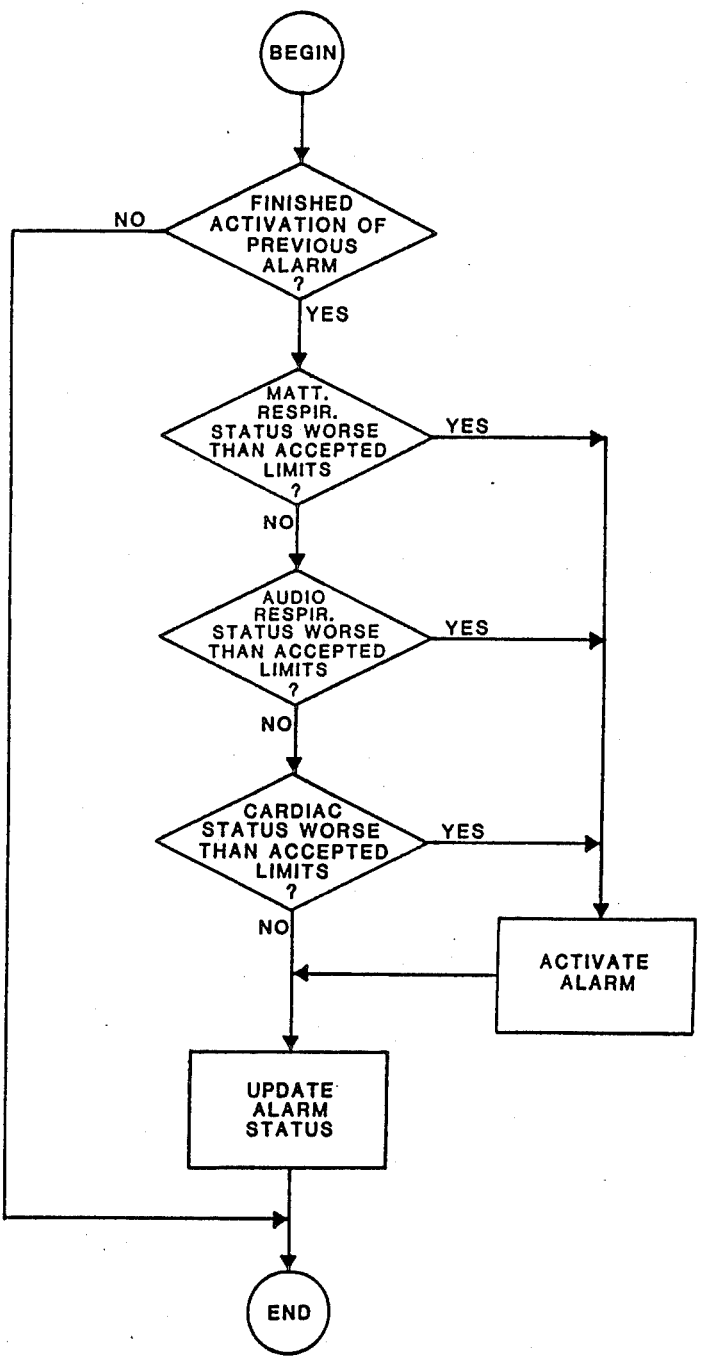
FIG. 6 is an expanded illustration of the signal processing logic for the alarm date circuit of FIG. 2.

In order of sampling, analysis and performance of gain check for each of the physiological activities illustrated in FIG. 2 has been simplified for the purposes of explanation. In reality, these activities are occurring concurrently along each of the separate channels. The signal processing logic of the system also performs analysis of these discrete channels concurrently and in real-time. Upon completion of sampling of these input signals for each of the monitored physiological activities, a qualitative evaluation of the signal sample for each physiological activity is performed by the alarm update system processing logic (FIG. 6). If such qualititative evaluation indicates abnormal activity, an alarm is triggered. An alarm can be of the type which dictates intervention to restore breathing; or, simply note an atypical signal or signal pattern without the need for intervention. The system's logic, thus, has the ability to effectively differentiate between many abnormal activity states (specifically denoting any event of interest) and alert the clinician or parent only to those events which require intervention. This monitor thus performs a true measurement function, instead of simply gauging (+) or (−) alarm states. This capability to discriminate between abnormal signal patterns also dramatically reduces the frequency of false alarms and, thus, enhances the credibility of the monitor.

Figure 3A:
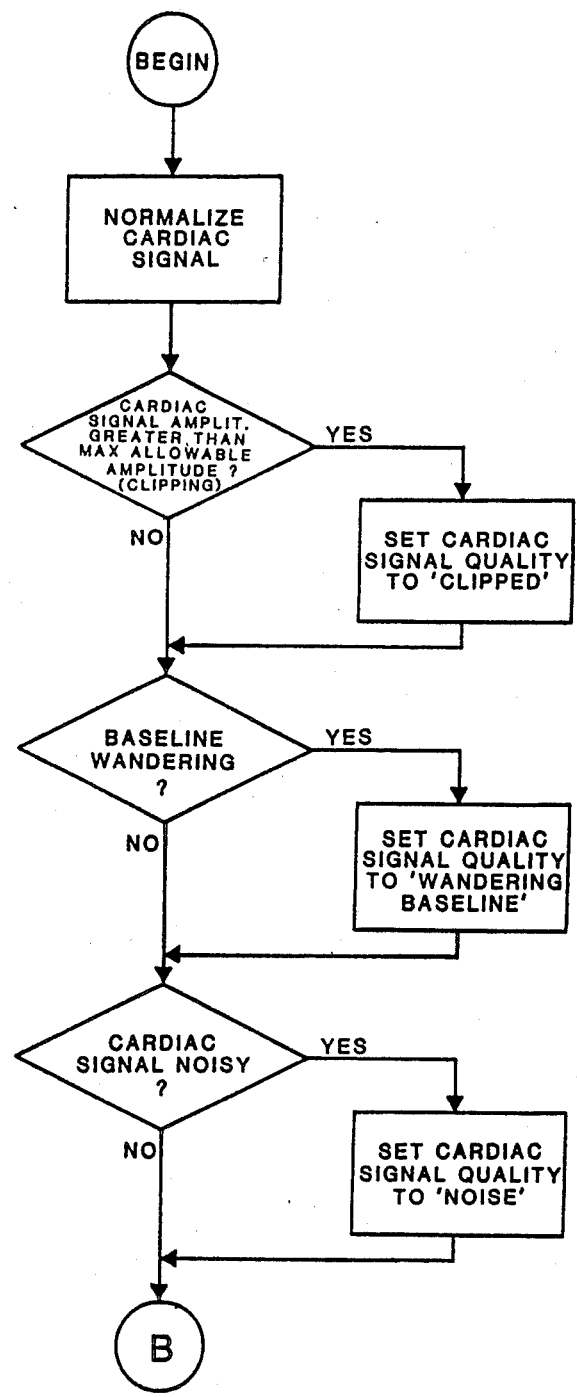
FIG. 3A is an expanded illustration of the cardiovascular signal processing logic of FIG. 2.
Figure 3B:
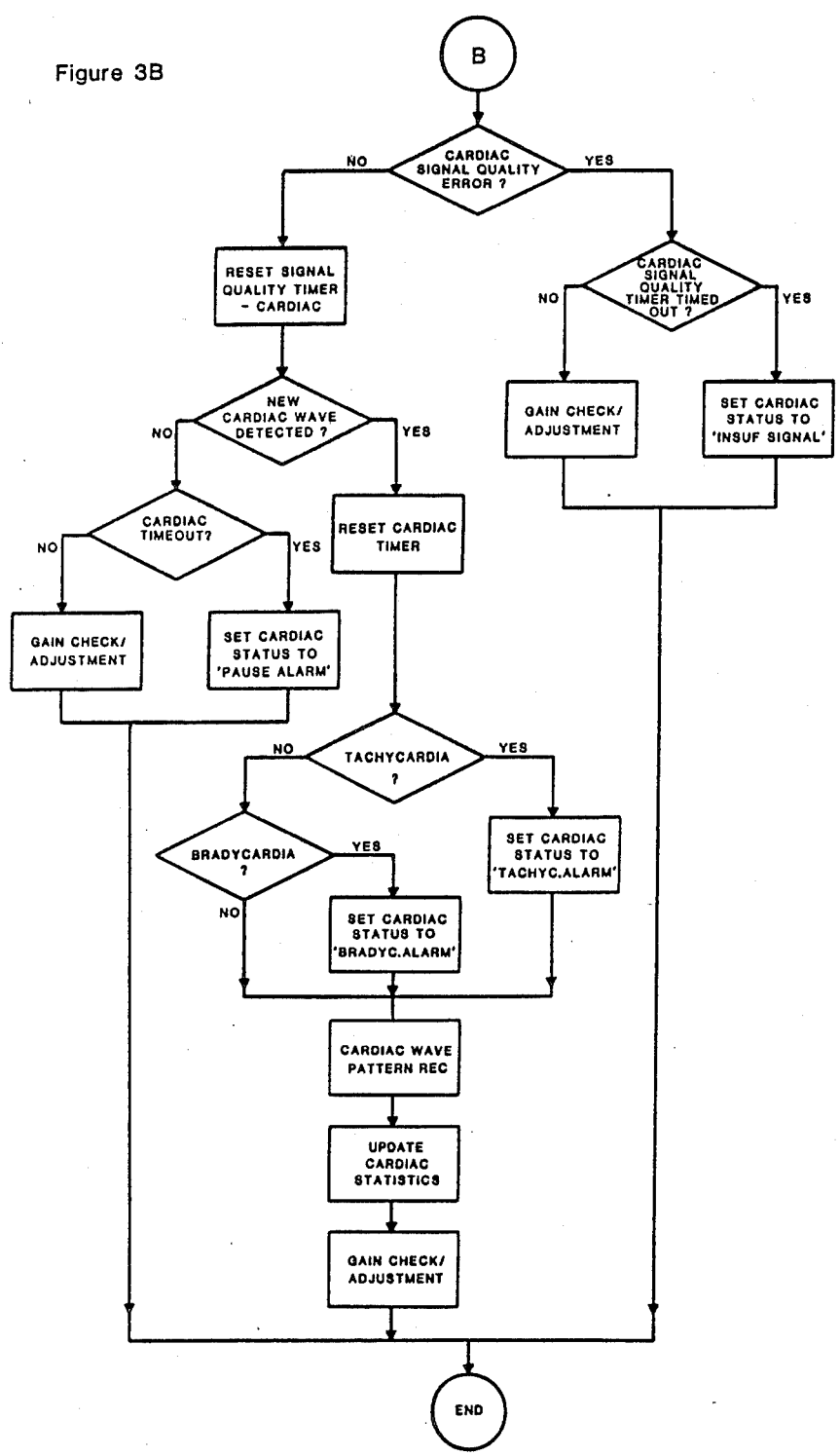
FIG. 3B is a continuation of the cardiovascular signal processing logic from point B of FIG. 3A.

FIGS. 3A and 3B provide an expanded illustration of the system processing logic for the cardiac signal input. Because of the relatively complex system processing logic involved with this physiological activity, this activity has required illustration in two separate figures, FIG. 3A and FIG. 3B. It should be emphasized that this cardiac signal (ballistic cardiogram—BCG) is derived from the subtle movements associated with cardiovascular activity. The transducer used to detect such movement is the same as used to detect movement associated with respiratory activity.

In brief, the cardiac signal system processing logic initially undergoes "normalization" of the signal input to confirm that the signal is within the range of the analog/digital converter. This is achieved by accentuation of the wave form of interest through the application of certain software filters. If the gain has been improperly set, or the physiological activity is more intense than anticipated, the amplitude of the signal may be of too great a magnitude to be accurately monitored. In order to avoid "clipping" of the signal and restore signal amplitude to within the digitizing range, the gain is adjusted accordingly. Similarly, where the system base line is wandering, this is noted so that it may be corrected to insure the appropriate basis of comparison of the amplitude of signal input to data stored in the microprocessor.

FIG. 3B is a continuation of FIG. 3A from point B. Once the signal has been normalized, the cardiac signal can then be qualitatively evaluated. In the event the cardiac signal quality is poor (e.g. clipped, wandering or noisy) or weak, the system logic will make a gain check adjustment, reset itself, and sample an additional data set. If poor input signal quality persists, the system logic will initiate an alarm sequence indicative of a system malfunction. Where the quality of the cardiac signal is acceptable based upon comparison to established parameters, the system logic is reset for sampling the next set of cardiac signal data. For each new wave of cardiac input data which is detected, the cardiac signal quality timer is reset. Where there is a significant interval between detection of successive cardiac waves, a second gain check adjustment is made and if no new cardiac wave is detected within the interval (parameter) for the cardiac time out, the system logic will set the cardiac status to insufficient signal. Where the cardiac status is determined by the alarm update system logic to be unacceptable, an alarm will be activated.

Assuming that the cardiac signal quality is within acceptable limits and there is essentially continuous flow of new cardiac signal data, the cardiac rate can then be compared to the parameters set by the physician or parent. If the rate is too high (tachycardia) the system logic will set the cardiac status to tachycardia alarm. If the heart rate is too low, (bradycardia), the system logic will set the cardiac status to bradycardia alarm. Where the rate of cardiac input is within the parameters set for the monitored activity or preceived to be abnormal, the system logic will perform a gain check adjustment. The shape/pattern of the wave form of the cardiac signal is then analyzed for features which characterize a given wave (period and amplitude), and comparisons made to wave forms of prior cardiac data. Such comparison of characteristic features of the wave form enable the monitor to effectively distinguish between data which is artifact from true cardiac signals. These characteristic wave features are also reviewed by the system logic in its evaluation and identifications of cardiac signal trends. The system logic then proceeds to update the cardiac statistics by averaging the recently obtained data with that previously acquired. It is this averaging of data which enables the system logic to predict trends in cardiac activity and dynamically adjust the gain accordingly.

Figure 4A:
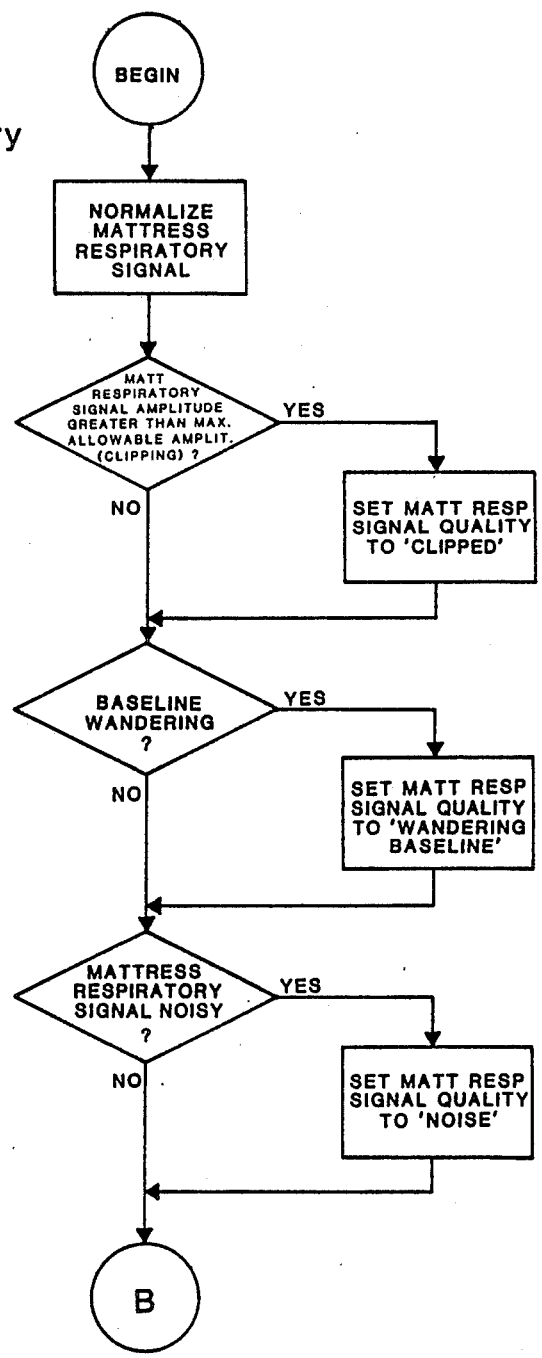
FIG. 4A is an expanded illustration of the mattress signal processing logic of FIG. 2.
Figure 4B:
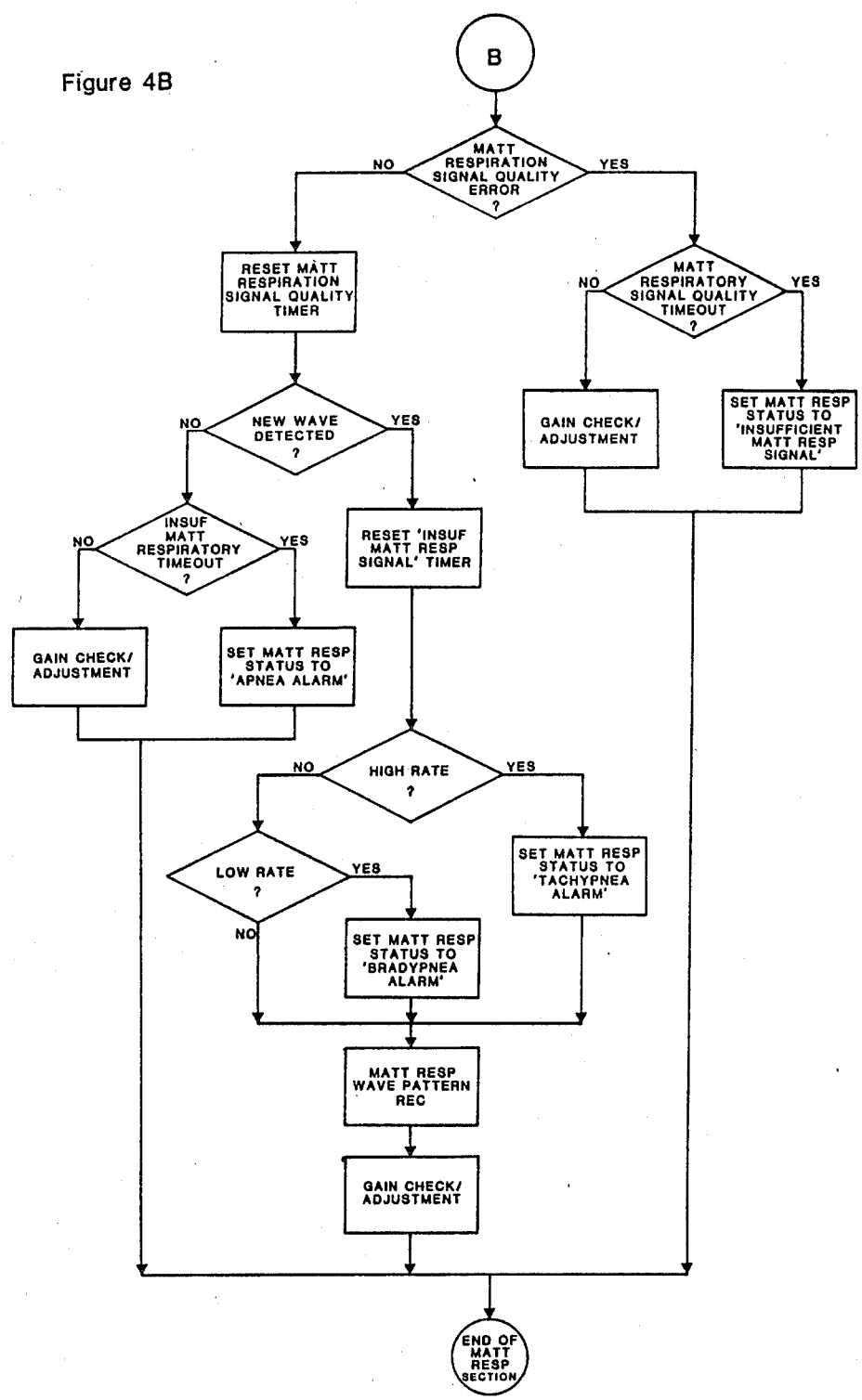
FIG. 4B is a continuation of the mattress signal processing logic from point B of FIG. 4A.

FIG. 4A and FIG. 4B provide an expanded illustration of the mattress respiratory signal processing logic of FIG. 2. Because of the relative complexity of illustration of this physiological activity, such activity has required expression in two separate figures. FIG. 4A illustrates the system logic for "normalization" of the mattress respiratory signal to insure that it is within the range of the analog/digital converter. This process of normalization is analogous to that previously described in the discussion involving the normalization of the cardiac input signal and, thus, need not be repeated here. The system logic of FIG. 4A performs necessary corrections and adjustments (if any) before the mattress respiratory signal can be qualitatively evaluated.

Once these adjustments are effected, to the extent required, the mattress respiratory signal quality is evaluated. Where the signal is clipped, wandering or noisy, the system logic will make a gain check adjustment, reset itself and sample an additional data set. If poor respiratory input signal quality persists, the system logic will set the respiratory status as indicative of a system malfunction (insufficient mattress respiratory signal).

Where the quality of respiratory mattress signal is perceived as adequate, the system logic is reset for sampling of the next set of mattress respiratory data. For each new wave of mattress respiratory data which is detected, the mattress respiratory signal quality timer is reset. Where there is a relatively long interval between detection of successive mattress respiratory waves, a second gain check adjustment is made and if no new mattress respiratory wave is detected within the interval for the mattress respiratory time out, the system logic will set the mattress respiratory status to apnea alarm. If the mattress respiratory status is determined by the alarm update system logic to be outside of accepted limits set for respiratory activity, an alarm will be activated.

Assuming that mattress respiratory signal quality is within acceptable limits and there is an essentially continuous flow of new mattress respiratory signal data, the mattress respiratory rate can then be compared to parameters set by the physician or parent. If the respiratory rate is too high (tachypnea), the system logic will set the mattress respiratory status to tachypnea alarm. If the respiration rate is too low, (bradypnea) the system logic will set the mattress respiration status to bradypnea alarm. The shape/pattern of the wave form of the respiratory signal is analyzed for features which characterize a given wave (i.e. period and amplitude), and comparison made to the wave form of prior respiratory data. Such comparison of the characteristic features of the wave form enable the monitor to effectively distinguish between data which is artifact from true respiratory signals. The characteristic wave features are also received by the system logic in its evaluation of and identification of respiratory signal trends. For example, this pattern recognition of the wave form of the respiratory signals enables characterization of a sequence of respiratory waves as representative of normal breathing or as representative of a pathological breathing pattern, e.g. Cheyne-Stokes breathing. Whether the respiration rate is within the parameters set for the monitored activity or perceived to be abnormal, the systen logic will perform a gain check adjustment.

Figure 5:
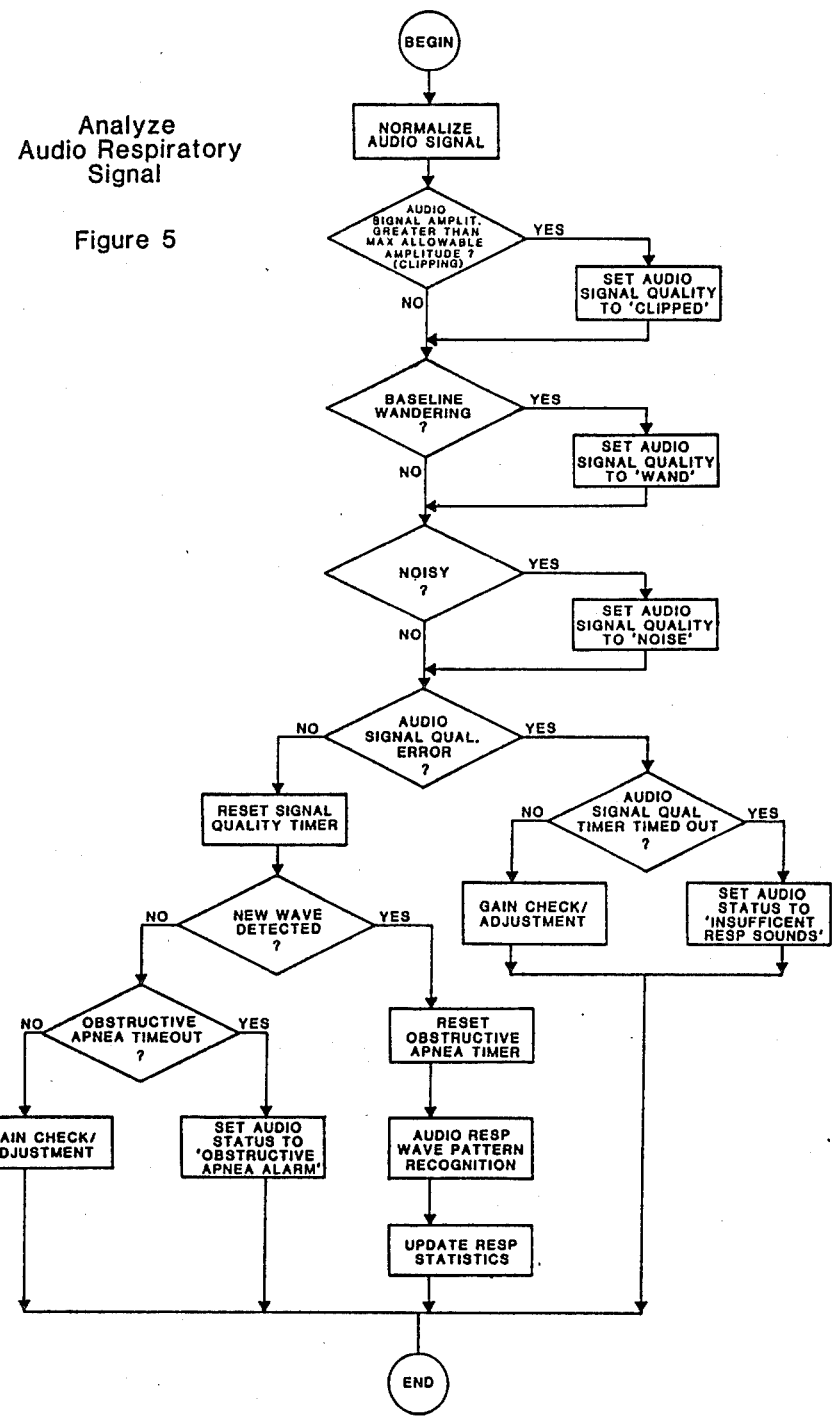
FIG. 5 is an expanded illustration of the audio-respiratory signal processing logic of FIG. 2.

FIG. 5 is an expanded illustration of the audio-based respiratory signal processing logic of FIG. 2. This signal is derived from the LPC coefficients discussed previously. In brief, the audio-based respiratory signal is "normalized" to insure that it is within the range of analog to digital convertor. This normalization process is analogous to that previously described for the cardiac input signal and, thus, need not be repeated. Once the signal has been normalized, it is qualitatively evaluated. This qualitative evaluation involves determination of the strength and adequacy of the signal and execution of a gain check adjustment. If a weak or an inadequate signal persists, the system logic will set the audio status to indicate an insufficient audio-based respiratory signal. Where, however, the audio-based respiratory signal is deemed adequate, the system logic is reset for sampling the next set of audio-based respiratory data. The system logic will then reset the signal quality timer and sample an additional data set. For each new wave of audio-based respiratory data which is detected, the audio respiratory signal quality timer is reset. Where there is a relatively long interval between detection of successive audio respiratory waves, a second gain check adjustment is made. If no new audio-based respiratory wave is detected within the interval for the obstructive apnea timeout, the system logic will set the audio-based respiratory status to obstructive apnea alarm. If the audio-based respiratory signal status is determined by the alarm update system logic to be outside of the accepted limits set for the audio respiratory activity, an alarm will be activated. Assuming that the audio-based respiratory signal is within acceptable limits and there is essentially a continuous flow of new waves of new audio-based respiratory signal data, the obstructive apnea timer will be reset. The system logic will also use the acceptable mattress and audio-based respiratory signal data to update the respiratory statistics in the microprocessor memory. Such updating of statistics enables the microprocessor to plot trends in such data.

FIG. 6 is an expanded illustration of the alarm update signal processing logic of FIG. 2. In brief, the alarm update simply checks the mattress and audio respiratory status alarm. If the respiratory signal is perceived to be abnormal, an alarm is activated by the alarm update system logic. Similarly, the alarm update system logic checks the cardiac status alarm. If any unusual status has been set, then an alarm is activated. The system logic can also assign alarm state priorities. In the preferred configuration of the system of this invention, the system logic will "arbitrate" between different alarm states before implementing a decision to initiate an alarm.

Figure 7:
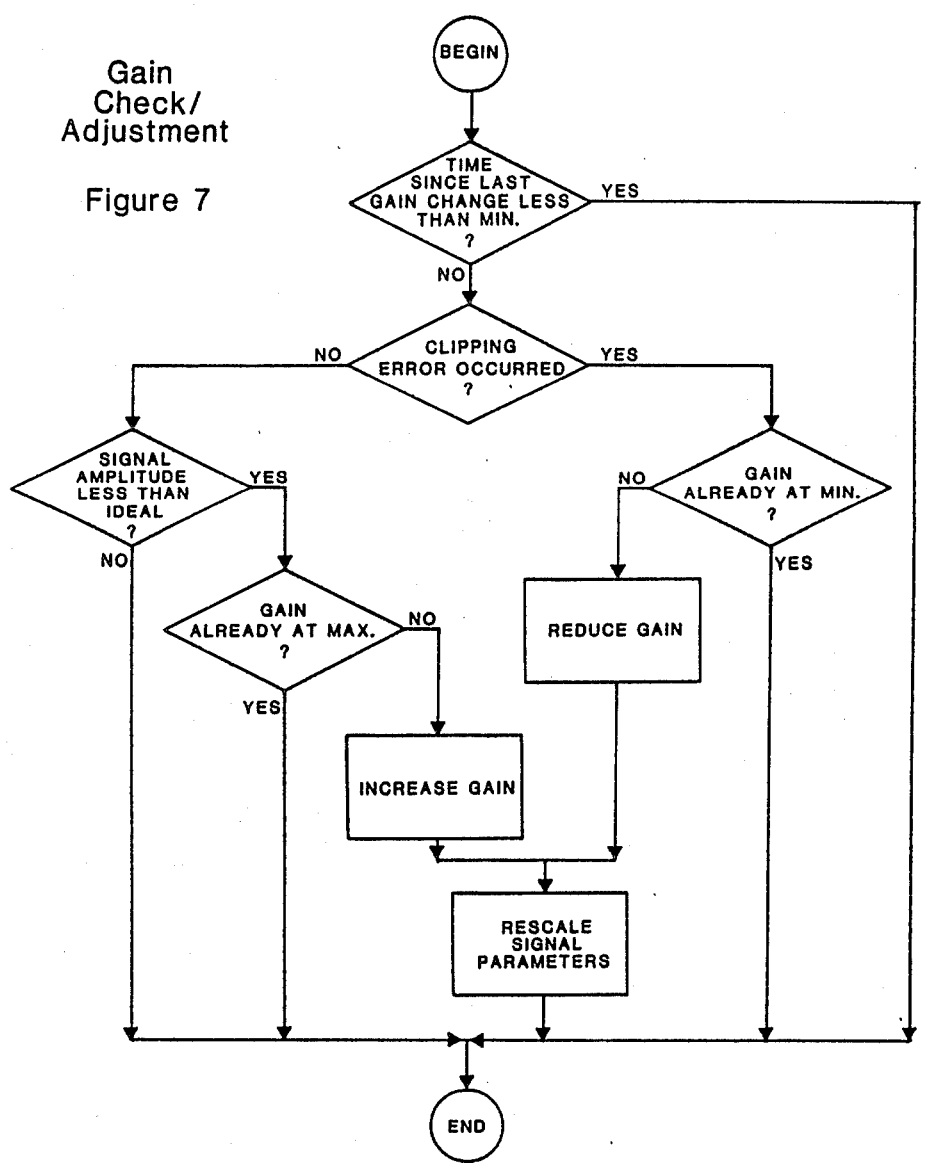
FIG. 7 is an expanded illustration of the signal processing logic for the gain check adjustment of FIG. 2.

FIG. 7 is an expanded illustration of the signal processing logic for the gain check adjustment of FIG. 2. The signal processing logic of the gain check adjustment will initially determine when the last gain check was made. If a prescribed time interval has expired, the system will perform a gain check in order to confirm that the data sampling is occurring within the parameters set for the system. The system will also check to determine if a clipping error has occurred since the last gain check; namely, whether or not a portion of the signal is outside the parameters set for the signal by the system. If in fact clipping is occurring, the system logic will determine if the gain is already at the minimum. If in fact it is at the minimum, no further gain reduction can be performed. If the gain is not at the minimum when clipping is detected, the system logic will reduce the gain and then rescale the signal parameters accordingly. Where no clipping of the signal is occurring, the system logic will determine if the signal amplitude is less than ideal for the sampling of the input data. Where the signal amplitude is less than ideal and the gain is already set at its maximum, no further gain increase can be performed. Where the gain is not at the maximum and the signal amplitude is less than ideal, the system logic will increase the gain and then rescale the signal parameters accordingly. Where the signal amplitude is set within the range set for such parameters, the signal parameters will not be rescaled. The gain check adjustments are permitted by the above system logic only when such changes can be made without triggering an erroneous alarm, i.e., when the signal it at or near the base-line, (zero voltage).

The information (data sets) upon which the above system logic operates, is generated by a transducer within the mattress of the monitor and one or more microphones which have been strategically positioned to receive audible sounds indicative of breathing activity. The mattress transducer suitable for use in the device of this invention is of the type described in Lewiner et al, U.S. Pat. No. 4,359,726. The preferred configuration of this device incorporates a piezoelectric film of polyvinylidene fluoride. This transducer is capable of sensing the motion associated with both respiratory and cardiovascular activity (ballistic cardiogram).

The detection of audible sounds associated with breathing/choking can be accomplished with one or more microphones which have been strategically positioned relative to the monitored subject. Where, a single microphone is used, its design and placement need be more exact so as to focus its sound-collection capabilities upon the source of acoustic input. This can be achieved through design of the microphone itself (i.e. parabolic microphone) or by shielding the monitored field from extraneous sounds.

Alternatively, the detection of audible sounds can be achieved with a microphone array. With this type of microphone configuration, it is possible to emphasize the desirable acoustic information while at the same time attenuating and/or distorting the unwanted speech or random noise. This is achieved by application of well-known nonlinear signal processing techniques (either preprocessing the analog signals or utilizing techniques that are classified as digital signal processing) to the outputs of two or more microphones (known as a microphone array). The processing of the microphone signals, results in an output signal which enhances the on-center (crib) sounds. This class of nonlinear signal processors, for the outputs of an array of microphones, emphasizes sounds coming from a particular (on-center) location against a background of other sounds. These processes completely eliminate any off-center impulsive noise which is non-overlapping at the microphones.

The approach of deriving a single audio signal, via analog preprocessing, depends upon each microphone in the array simultaneously receiving the wanted signal, thus requiring delay and gain adjustments unless the effects of these parameters are negligible. If the effects of gain and delay are not negligible, then digital signal processing is required. The digital signal processing of a microphone array permits the delay and gain adjustments to be mathematically performed by the computer program.

In a ventilation monitor of the type contemplated by this invention, the array processor utilizes a variation of the class of nonlinear signal processors described in an article by O. M. M. Mitchell, et. al., "Signal Processing for a Cocktail Party Effect", J. Acoustic Sco. Amer. Vol. 50, No. 2 (Part 2), pp. 656–660, August 1971. The output signal of a nonlinear processor of this type is given by the equation:

$$S = v1 + v2 + v3 + v4 - |v1 - v2| - |v3 - v4| + |v1 + v2 - v3 - v4 - |v1 - v2| + |v3 - v4||$$

where v1, v2, v3, and v4 are the four (4) microphone inputs.

The output appears complicated, but the output S is always exactly equal to four times sum of the inputs and is given by the following relations:

$$s1 = \min(v1, v2)$$

and $$s2 = \min(v3, v4)$$

thus $S = 4*\max(s1, s2)$.

The above relationships expressed in the foregoing equations may be summarized as follows: the output S is four times the greater of two quantities s1 and s2; where s1 is the lessor of the inputs v1 and v2, and s2 is the lessor of the inoputs v3 and v4. In effect, the nonlinear processor "looks" at only one input at a time and ignores all of the others.

In addition to the motion and acoustic sensors described above, this system is compatible with other sensors commonly used for monitoring physiological activities associated with respiration and other vital physiological functions. For example, the above device can also incorporate and process information obtained from additional sensors such as an impedance belt, transcutaneous sensors, (for PO2 and PCO2) and a thermometer. It is to be emphasized that these additional sensors are not contemplated as a replacement for either the motion or acoustic sensors described previously. As will also be appreciated, these additional sensors require (to a greater or lessor degree) more intimate physical contact with the monitored subject than do the preferred motion and acoustic sensors of the device previously described. Under certain circumstances, it may, however, be desirable to incorporate the motion sensor of the preferred device into a harness to be worn by the monitored subject. For example, when the monitored subject is to be taken out of the hospital or home environment, a motion sensor incorporated within a harness, in conjunction with a portable monitor, may be the only practical way to maintain continuous surveillance of the monitored subject, (i.e. an infant). Of course, if the remote environment (i.e. carriage) were equipped with a motion sensor within a mattress, such a harness would be unnecessary.

Figure 8:
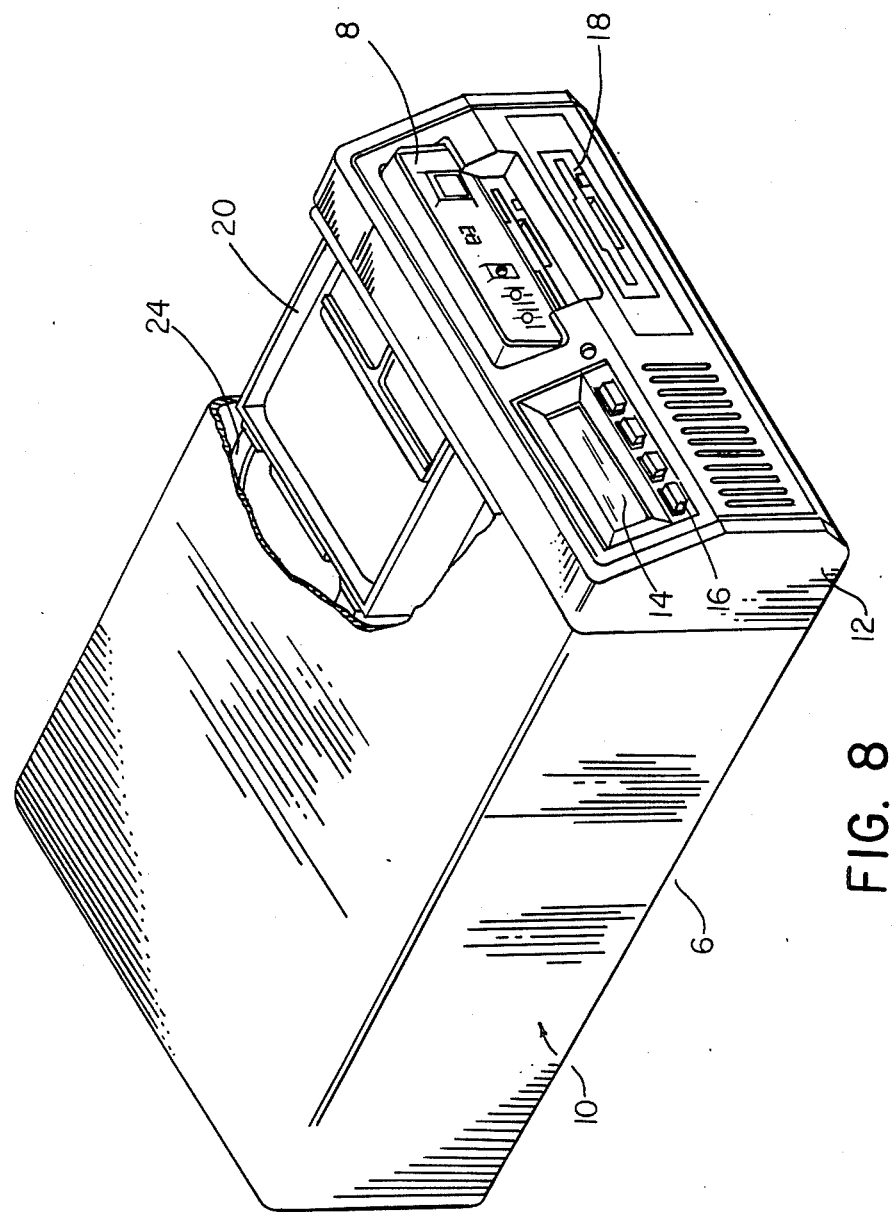
FIG. 8 is a perspective view of an embodiment of the monitor of this invention which incorporates a base station and a portable unit in docking relation to one another.

In order to permit a degree of mobility to the monitored subject, the most preferred ventilation monitor of this invention contemplates both an integrated main, or base station (6) and a modular, or portable unit (8), of the type illustrated in FIG. 8. The main unit of the monitor illustrated in FIG. 8 includes a housing (10) for the electronic circuitry and microprocessor (not shown) which are required to process the data acquired during the monitoring of the patient. The front panel (12) of the housing (10) includes a display (14), function keys (16), accommodation (18) for a tape drive recorder (not shown) and accommodation (20) for docking a portable monitor (8). This portable monitor (8) is maintained within the main unit (6) during monitoring in the home or hospital environment. The main and portable units are maintained in a communicative relationship to one another via a ribbon connector (24) so as to insure that the microprocessor within each such unit is kept current as to the data associated the respiratory movements of the monitored subjects. Accordingly, when the patient is to be removed from the hospital or home environment, the portable unit (8) will be able to provide continuous monitoring of the patient. When a patient has returned to the hospital or home environment, the portable unit is redocked with the main station and all data recorded by the portable unit communicated to the microprocessor of the main station. Thus, the most preferred embodiment of this invention provides an effective means for continuous monitoring of the patient both in the environment of the base station and at a location which is remote from the base station.

The ventillation monitor of this invention also contemplates the utilization of additional pieces of peripheral equipment. For example, in the event an alarm state is detected, the microprocessor of the main unit has the capacity to communicate such information to a remote terminal. In addition, a separate tape drive can also be wired to the main unit to record data on the monitored subject or transmit such data via a modem to a computer or tape drive at a remote location.

As is evident from the foregoing description, the ventilation monitor of this invention possesses a degree of versatility and sophistication presently unavailable in prior art systems. It is, however, apparent that certain changes, additions or improvements may be made to this device without departure of the spirit or scope of this invention, which is set forth in the following claims.

What is claimed is:

1. A multi-channel ventilation monitor for real-time monitoring of multiple physiological activities associated with respiration of a monitored subject, involving comparison of a plurality of discrete data signals indicative of each such activity, said monitor comprising, in combination:
   (a) a plurality of sensors for detection of discrete physiological activity indicative of breathing activity, each of said sensed physilogical activity being converted by a transducer to data signals which are characteristic of the sensed physiological activity;
   (b) a plurality of discrete information processing channels for processing of the physiological data signal from each sensor, each such physiological data signals being processed in a separate channel;
   (c) a signal processing means for each such channel for verifying the quality of each such signal;
   (d) means for dynamic adjustment of the gain and frequency response for each of the sensed physiological activity to reflect trends in the data signal for each such physilogical activity;
   (e) means for comparison of the wave form of each such signal to certain standards, including wave forms of a sensed physilogical activity which have been stored in a data base and wave forms of sensed physiological activity which are indicative of a trend in a sensed activity for the monitored subject; and
   (f) means for generation of an output signal to indicate abnormal physilogical activity associated with respiration.

2. The monitor of claim 1, wherein the sensors include a motion detector, contained within a mattress, and an acoustic sensor for detection of audible sounds indicative of breathing activity.

3. The monitor of claim 1, wherein the adjustment in the gain of the data signal for each of the sensed physiological activities is in response to changes in the level of the sensed physiological activity.

4. The monitor of claim 1, wherein the comparison of the wave form of the signal data to wave forms which are stored in a data base enables the monitor to effectively differentiate between a data signal which is indicative of a sensed physiological activity and a data signal which is artifact.

5. The monitor of claim 1, further including:
   (a) means for assignment of priorities among the various perceived abnormal activity states; and
   (b) means for arbitration between the various abnormal activity states, based upon assignment of priorities, prior to the initiation of an alarm.

6. A multi-channel ventilation monitor for real-time monitoring of multiple physiological activities associated with respiratory and cardiovascular movement of a monitored subject, involving comparison of a plurality of discrete data signals indicative of each such activity, said monitor comprising, in combination:
   (a) a plurality of sensors, at least one of which being provided for detection of movement indicative of respiratory activity and for detection of movement indicative of cardiovascular activity, each of said sensed physiological activity being converted by a transducer to data signals which are characteristic of each of the sensed physiological activity;
   (b) a plurality of discrete information processing channels for processing the physiological data signals from each sensor, each such physiological data signals being processed in a separate channel;
   (c) a signal processing means for each such channel for verifying the quality of each such signal;
   (d) means for dynamic adjustment of the gain and frequency response for each of the sensed physiological activity to reflect trends in the data signal for each such physiological activity; and
   (e) means for comparison of the wave form of each such signal to certain standards, including wave forms of a sensed physiological activity which have been stored in a data base and wave forms of sensed physiological activity which are indicative of a trend in a sensed activity for the monitored subject; and (f) means for generation of an output signal indicative of abnormal movement associated with breathing and/or cardiovascular activity.

7. The monitor of claim 6, wherein the sensors include a motion detector, contained within a mattress, and an acoustic sensor for detection of audible sounds indicative of breathing activity.

8. The monitor of claim 6, wherein the adjustment in the gain of the data signal for each of the sensed physiological activities is in response to changes in the level of the sensed physiological activity.

9. The monitor of claim 6, wherein the comparison of the wave form of the signal data to wave forms which are stored in a data base enables the monitor to effectively differentiate between a data signal which is indicative of a sensed physiological activity and a data signal which is artifact.

10. A multi-channel ventilation monitor for real-time monitoring of multiple physiological activities indicative of respiration by measurement of the immediate ambient environment of the monitored patient for discrete data signals indicative of each such activity state, said monitor comprising, in combination:
(a) a plurality of sensors for detection, within the immediate ambient environment of the monitored subject, discrete physiological activity indicative of breathing activity, each of said sensed physiological activity being converted by a transducer to signal data which are characteristic of the sensed physiological activity;
(b) a plurality of discrete information processing channels for processing the physiological data signals from each sensor, each such physiological data signals being processed in a separate channel;
(c) a signal processing means for each such channel for verifying the quality of each such signal; (d) means for dynamic adjustment of the gain and frequency response for each of the sensed physiological activity to reflect trends in the data signal for each such physiological activity; and
(e) means for comparison of the wave form of each such signal to certain standards, including wave forms of a sensed physiological activity which have been stored in a data base and wave forms of sensed physiological activity which are indicative of a trend in a sensed activity for the monitored subject; and
(f) means for generation of an output signal to indicate abnormal respiratory activity.

11. The monitor of claim 10, wherein the sensors include a motion detector, contained within a mattress, and an acoustic sensor for detection of audible sounds indicative of breathing activity.

12. The monitor of claim 10, wherein the adjustment in the gain of the data signal for each of the sensed physiological activities is in response to changes in the level of the sensed physiological activity.

13. The monitor of claim 10, wherein the comparison of the wave form of the signal data to wave forms which are stored in a data base enables the monitor to effectively differentiate between a data signal which is indicative of a sensed physiological activity and a data signal which is artifact.

14. In a method for real-time monitoring of multiple physiological activities indicative of respiration of a monitored subject, involving sensing of the physiological activity, generation of a data signal indicative of such physiological activity, processing of the data signal and comparison of the data signal to certain standards and/or physician defined parameters, the improvement comprising:
(a) providing
(i) a plurality of sensors for detection of discrete physiological activity indicative of breathing activity, each of said sensed physiological activity being converted by a transducer to data signals which are characteristic of the sensed physiological activity;
(ii) a plurality of discrete information processing channels for processing the physiological data signals from each sensor, each such physiological data signals being processed in a separate channel; and
(iii) a signal processing means for each such channel for verifying the quality of each such signal;
(b) sensing a plurality of physiological activities indicative of breathing activity and generating data signals indicative of each such activity;
(c) dynamically adjusting the gain and frequency response for each of the sensed physiological activity to reflect trends in the data signal for each such physiological activity;
(d) comparing the wave form of each such signal to certain standards, including wave forms of a sensed physiological activity which have been stored in a data base and wave forms of sensed physiological activity which are indicative of a trend in a sensed activity for the monitored subject; and
(e) generating an output signal to indicate abnormal respiratory activity.

* * * * *